United States Patent [19]

Bright

[11] 4,124,755
[45] Nov. 7, 1978

[54] 11-ALKANOYL-4"-DEOXY-4"-ISONITRILO-OLEANDOMYCIN DERIVATIVES

[75] Inventor: Gene M. Bright, Groton, Conn.

[73] Assignee: Pfizer Inc., New York, N.Y.

[21] Appl. No.: 866,721

[22] Filed: Jan. 3, 1978

[51] Int. Cl.$^2$ .................. C07H 17/08; A01N 9/00
[52] U.S. Cl. ............................ 536/9; 536/17; 424/180
[58] Field of Search ............... 536/9, 17; 424/180

[56] References Cited

U.S. PATENT DOCUMENTS

| | | | |
|---|---|---|---|
| 3,869,445 | 3/1975 | Hallas et al. | 536/9 |
| 3,884,903 | 5/1975 | Jones et al. | 536/9 |
| 3,884,904 | 5/1975 | Jones et al. | 536/9 |
| 4,063,014 | 12/1977 | Hallas et al. | 536/9 |
| 4,069,379 | 1/1978 | Sciavolino | 536/9 |

Primary Examiner—Johnnie R. Brown
Assistant Examiner—Blondel Hazel
Attorney, Agent, or Firm—Francis X. Murphy; Charles J. Knuth; Albert E. Frost

[57] ABSTRACT

11-Alkanoyl-4"-deoxy-4"-isonitrilo-oleandomycin antibacterial agents and their synthesis from 11-alkanoyl-4"-deoxy-4"-formamido-oleandomycins.

2 Claims, No Drawings

11-ALKANOYL-4"-DEOXY-4"-ISONITRILO-OLEANDOMYCIN DERIVATIVES

BACKGROUND OF THE INVENTION

1. Field of the Invention

This invention relates to novel antibacterial agents and, in particular, to 11-alkanoyl-4"-deoxy-4"-isonitrilo-oleandomycins and their pharmaceutically acceptable acid addition salts.

2. Description of the Prior Art

Oleandomycin, its production in fermentation broths and its use as an antibacterial agent was first described in U.S. Pat. No. 2,757,123. The naturally occurring compound is known to have the following structure:

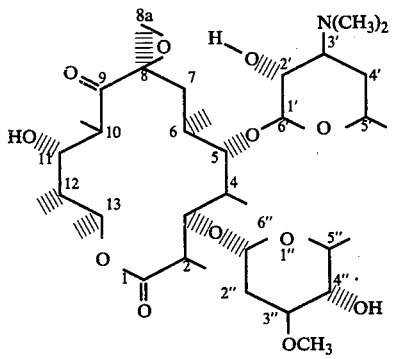

The conventionally accepted numbering shceme and stereochemical representation for oleandomycin and similar compounds is shown at a variety of positions.

Several synthetic modifications of this compound are known, particularly those in which from one to three of the free hydroxyl groups found at the 2', 4" and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

SUMMARY OF THE INVENTION

The semi-synthetic oleandomycin compounds of this invention are of the formula:

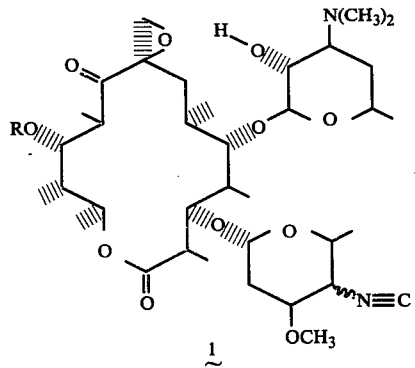

and a pharmaceutically acceptable acid addition salt thereof wherein R is alkanoyl having from two to three carbon atoms.

Especially preferred as an antibacterial agent is the compound wherein R is acetyl.

The stereochemistry of the starting materials leading to the antibacterial agents of the present invention is that of the natural material. Oxidation of the 4"-position of the natural oleandomycin derivatives leads to the 4"-ketone. Reductive amination of the 4"-oxo compounds presents an opportunity for the stereochemistry of the 4"-amino group to be different from the natural product. The absolute stereochemistry of the 4"-amino group and the 4"-isonitrilo, for which the amine is a starting material, has not yet been established.

DETAILED DESCRIPTION OF THE INVENTION

In accordance with the process for synthesizing the 11-alkanoyl-4"-deoxy-4"-isonitrilo-oleandomycin antibacterials related to 1 the following scheme is illustrative:

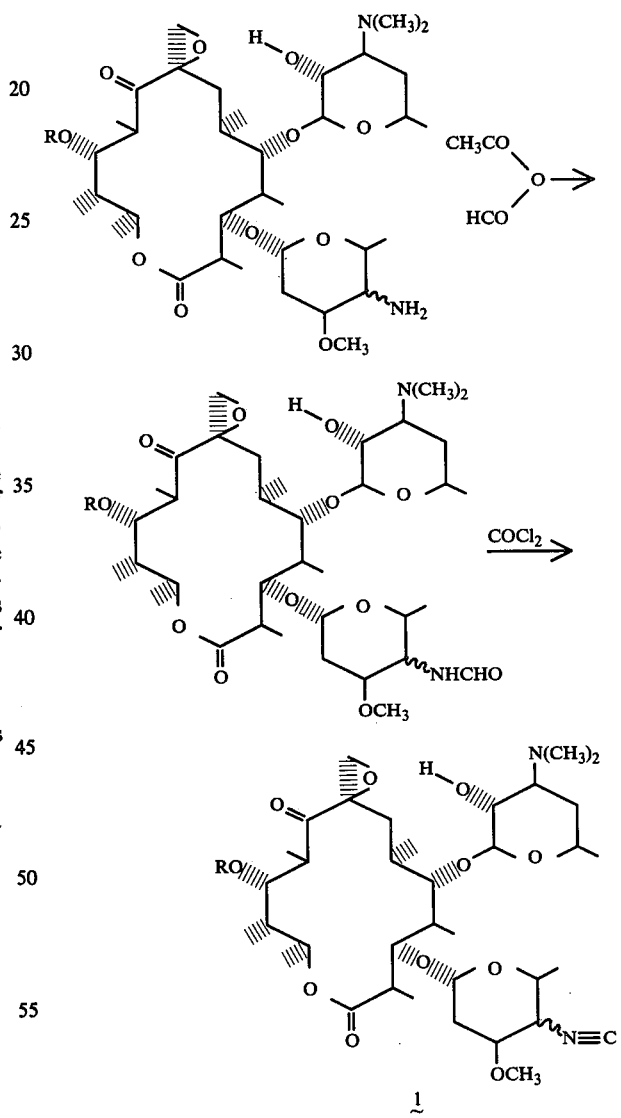

Acylation of the 4"-amino compound is effected using acetic-formic anhydride prepared according to the procedure of Olah, et al., *J. Org. Chem.*, 26, 225 (1961). One mole of the amine is contacted with one mole of the mixed anhydride in a reaction-inert solvent. Such solvents should appreciably solubilize the reactants while not reacting to any significant extent with either the starting reagents or the products formed.

Preferred are aprotic, polar solvents which are immiscible with water. Especially preferred are methylene chloride and chloroform.

It is preferred that the reaction be conducted at room temperature. At these temperatures the reaction is complete in 3–4 hours.

At the completion of the reaction, the organic solvent is treated with water, at a pH of about 9–10, to remove the acetic acid by-product. The organic phase containing the product is substantially washed, dried and concentrated to dryness. When a highly pure sample is desired, the product can be further purified by chromatographing on a silica gel column.

The formamido compound is converted to the antibacterial agent 1 by dehydration using phosgene. Experimentally, a solution of one mole of the formamide and five to six moles of a hydrogen chloride scavenger, such as triethylamine, in a chlorinated hydrocarbon solvent at 0° C. is treated with sufficient phosgene, dissolved in a similar solvent, to give the desired product. In order to determine the progress of the reaction, the samples are frequently removed and the aliquots subjected to infrared analysis. When the strong 1685 $cm^{-1}$ carbonyl band of the formamide completely disappears, with the concomitant appearance of the isonitrile band at 2140 $cm^{-1}$, the reaction is complete and no further phosgene addition is necessary.

At the completion of the reaction, the organic phase is washed several times with water and subsequently dried and concentrated to dryness.

The starting 4"-amino compounds used in the synthesis of antibacterial agents of the present invention are synthesized by oxidation of the natural oleandomycin followed by a reductive amination of the resultant ketone as hereinafter described.

In the utilization of the chemotherapeutic activity of those compounds of the present invention which form salts, it is preferred, of course, to use pharmaceutically acceptable salts. Although water-insolubility, high toxicity or lack or crystalline nature may make some particular salt species unsuitable or less desirable for use as such in a given pharmaceutical application, the water insoluble or toxic salts can be converted to the corresponding pharmaceutically acceptable bases by decomposition of the salt or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel 4"-deoxy-4"-isonitrilo-oleandomycin derivatives described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick room utensils; and as industrial antimicrobials, for example, in water treatment, slime control, paint and wood preservation.

For in vitro use, e.g., for topical application, it will often be convenient to compound the selected product with a pharmaceutically acceptable carrier such as vegetable or mineral oil or an emollient cream. Similarly, they may be dissolved or dispersed in liquid carriers or solvent, such as water, alcohol, glycols or mixtures thereof or other pharmaceutically acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive microorganisms via the oral and/or parenteral routes of administration in animals, including man. Their in vivo activity is more limited as regards susceptible organisms and is determined by the usual procedure which comprises mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 5 mg./kg. to about 200 mg./kg. of body weight per day. The favored dosage range is from about 25 mg./kg. to about 100 mg./kg. of body weight per day and the preferred range from about 50 mg./kg. to about 75 mg./kg. of body weight per day. Vehicles suitable for parenteral injection may be either aqueous such as water, isotonic saline, isotonic dextrose, Ringers' solution, or non-aqueous such as fatty oils or vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

11-Acetyl-4"-deoxy-4"-formamido-oleandomycin

To a solution of 4.0 g. (5.5 mmoles) of 11-acetyl-4"-deoxy-4"-amino-oleandomycin in 25 ml. of anhydrous methylene chloride at 25° C. is added 483 mg. (5.5 mmoles) of acetic-formic anhydride all at once. After 3 hrs. stirring at ambient temperatures, 150 ml. of methylene chloride and 150 ml. of water are added to the reaction. The pH of the aqueous phase is adjusted to 9.8 with 1N aqueous sodium hydroxide. The organic layer is separated, washed with water (2 × 150 ml.) and dried over sodium sulfate. Removal of the solvent in vacuo leaves a colorless foam, which on chromatographing on silica gel using acetone as the eluate affords the pure 2.26 g. of desired product.

NMR ($\delta$, CDCl$_3$): 2.09 (3H)s; 2.34 (6H)s; 2.69 (2H)m; 3.45 (3H)s; and 3.21 (1H) broad doublet.

In a similar manner is prepared 11-propionyl-4"-deoxy-4"-formamido-oleandomycin.

EXAMPLE 2

11-Acetyl-4"-deoxy-4"-isonitrilo-oleandomycin

To a solution of 100 mg. (0.13 mmoles) of 11-acetyl-4"-deoxy-4"-formamido-oleandomycin and 1 ml. (7 mmoles) of triethylamine in 5 ml. of methylene chloride at 0° C. is added dropwise a 0.41M of phosgene in chloroform. Frequent infrared monitorings of the reaction mixture are made to determine sufficient volume of phosgene solution to cause disappearance of 1685 cm$^{-1}$ formamido carbonyl resonance of the starting material, with concomitant appearance of isonitrile resonance at 2140 cm$^{-1}$. The reaction mixture is then diluted with 100 ml. of methylene chloride, washed with water (4 × 150 ml.) and dried over sodium sulfate. Removal of the solvent under reduced pressure affords 94 mg. of the desired product.

NMR ($\delta$, CDCl$_3$): 2.09 (3H)s; 2.29 (6H)s; 2.69 (2H)m; and 3.46 (3H)s.

In a similar manner is prepared 11-propionyl-4"-deoxy-4"-isonitrilo-oleandomycin

PREPARATION A

4"-Deoxy-4"-amino-oleandomycins

I. 11-Acetyl-4"-deoxy-4"-oxo-oleandomycin a. 11,2'-Diacetyl-4"-deoxy-4"-oxo-oleandomycin To a 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 min., the contents are cooled to −25° C. and treated with 5.0 g. of 11,2'-diacetyl-oleandomycin in 100 ml. of toluene. Cooling and stirring are continued for 2 hrs. followed by the addition of 4.73 ml. of triethylamine. The reaction mixture is allowed to stir at 0° C. for 15 min., and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR ($\delta$,CDCl$_3$): 3.48 (3H)s; 2.61 (2H)m; 2.23 (6H)s and 2.03 (6H)s.

b. 11-Acetyl-4"-deoxy-4"-oxo-oleandomycin

A solution of 4.0 g. of 11,2'-diacetyl-4"-deoxy-4"-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°–117° C.

NMR ($\delta$, CDCl$_3$): 3.43 (3H)s; 2.60 (2H)m; 2.23 (6H)s and 2.01 (3H)s.

Similarly, by employing 11,2'-dipropionyl-4"-deoxy-4"-oxo-oleandomycin or 11-propionyl-2'-acetyl-4"-deoxy-4"-oxo-oleandomycin in the above procedure, 11-propionyl-4"-deoxy-4"-oxo-oleandomycin is prepared.

II. 11-Acetyl-4"-deoxy-4"-amino-oleandomycin

To a suspension of 10 g. of 10% palladium-on-charcoal in 100 ml. of methanol is added 21.2 g. of ammonium acetate and the resulting slurry is treated with a solution of 20 g. of 11-acetyl-4"-deoxy-4"-oxo-oleandomycin in 100 ml. of the same solvent. The suspension is shaken at room temperature in a hydrogen atmosphere at an initial pressure of 50 p.s.i. After 1.5 hrs., the catalyst is filtered and the filtrate is added with stirring to a mixture of 1200 ml. of water and 500 ml. of chloroform. The pH is adjusted from 6.4 to 4.5 and the organic layer is separated. The aqueous layer, after a further extraction with 500 ml. of chloroform, is treated with 500 ml. of ethyl acetate and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°–160° C.

NMR ($\delta$, CDCl$_3$): 3.41 (3H)s; 2.70 (2H)m; 2.36 (6H)s and 2.10 (3H)s.

The other epimer, which exists in the crude foam to the extent of 20–25%, is obtained by gradual concentration and filtration of the mother liquors.

In a similar manner, starting with 11-propionyl-4"-deoxy-4"-oxo-oleandomycin in the above procedure, gives 11-propionyl-4"-deoxy-4"-amino-oleandomycin.

What is claimed is:

1. A compound selected from the group consisting of:

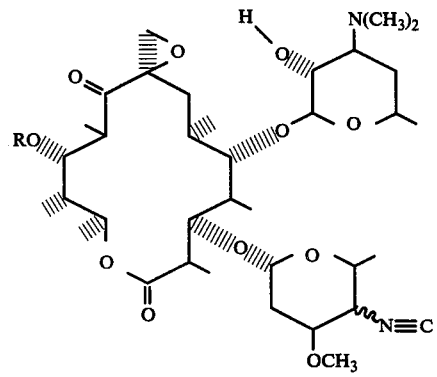

and a pharmaceutically acceptable acid addition salt thereof, wherein R is alkanoyl having from two to three carbon atoms.

2. The compound of claim 1 wherein R is acetyl.

* * * * *